United States Patent [19]
Du Toit

[11] Patent Number: 5,470,335
[45] Date of Patent: Nov. 28, 1995

[54] METHOD FOR CARRYING OUT AN OSTEOTOMY PROCEDURE

[75] Inventor: Guilluame T. Du Toit, Sandton, South Africa

[73] Assignee: Technology Finance Corporation (Proprietary) Limited, South Africa

[21] Appl. No.: 421,819

[22] Filed: Apr. 13, 1995

Related U.S. Application Data

[62] Division of Ser. No. 59,639, May 10, 1993, Pat. No. 5,413,579.

[30] Foreign Application Priority Data

May 13, 1992 [ZA] South Africa ............................ 92/3472

[51] Int. Cl.$^6$ .................................................. A61B 17/56
[52] U.S. Cl. .............................. 606/73; 606/82; 606/87; 606/96; 606/53
[58] Field of Search .................. 606/79, 82, 81, 606/87, 86, 96, 72, 73, 60, 53

[56] References Cited

U.S. PATENT DOCUMENTS 4,509,511  4/1985  Neufeld ................................ 606/82 X
4,627,425  12/1986  Reese .................................... 606/82 X
5,035,698  7/1991  Comparetto .............................. 606/82
5,042,983  8/1991  Rayhack .................................. 606/53

FOREIGN PATENT DOCUMENTS

1747046  7/1992  U.S.S.R. ................................. 606/53

Primary Examiner—Stephen C. Pellegrino
Assistant Examiner—Guy V. Tucker
Attorney, Agent, or Firm—Marshall, O'Toole, Gerstein, Murray & Borun

[57] ABSTRACT

A set of surgical instruments which comprises a saw guide and a drill guide respectively for guiding a saw blade cutting a bone and for guiding a drill bit for thereafter forming a passage in the bone. The saw guide has a seat formation for seating against the bone, and a guide formation for guiding the saw. The drill guide comprises a bit guide and an anchor to align the bit guide relative to the cut. Also provided are a saw guide and a drill guide; and a method of carrying out an osteotomy procedure by making an oblique cut through a long bone at a position where bone portions which are misaligned intersect each other to provide two bone fragments, whereafter they are loosely bolted together and then rotated about the axis provided by the bolting until the misalignment is reduced, after which they are bolted tightly together.

8 Claims, 6 Drawing Sheets

METHOD FOR CARRYING OUT AN OSTEOTOMY PROCEDURE

CROSS REFERENCE TO RELATED APPLICATION

This application is a divisional of U.S. application Ser. No. 08/059,639 filed May 10, 1993, now U.S. Pat. No. 5,413,579.

BACKGROUND OF THE INVENTION

1. Field of the Invention

THIS INVENTION relates to surgical instruments. More particularly it relates to a set of such instruments for use in an osteotomy procedure; to a saw guide and a drill guide forming part of the set; and to a method of carrying out an osteotomy procedure.

SUMMARY OF THE INVENTION

According to the invention there is provided, for use in an osteotomy procedure, a set of surgical instruments, the set comprising:

a saw guide for guiding a saw while it makes an oblique cut in a long bone to divide it into two fragments; and a drill guide for guiding a drill bit while it forms a passage in said bone after an initial part of said cut has been made in the bone by the saw, the saw guide and drill guide having respective constructions whereby:

the saw guide has a seat formation having a concave side for abutting a long bone to be cut, so that the long bone seats in the seat formation, and a guide formation for aligning a saw blade relative to a long bone seating in the seat formation and for guiding the saw blade while it initiates the making of the cut in the bone; and the drill guide comprises a bit guide and an anchor connected to the bit guide for insertion into the initial part of the cut in the bone when the initial part of the cut has been made, thereby to align the bit guide relative to the cut, the bit guide defining a guide path for receiving a drill bit and for aligning the drill bit perpendicular to the initial part of the cut while the drill bit forms the passage in the bone.

By an oblique cut is meant a transverse cut which is not substantially normal to the longitudinal direction of the bone.

In one embodiment, the saw guide may be in the form of a channel, which provides the seat formation. The guide formation may in this case be in the form of a slot in the channel, the slot extending transversely to the channel. The width of the slot will be selected to match the thickness of the blade of a standard hand-held hacksaw with a close working clearance, the hacksaw being operated by hand using a detachable handle, as motor-driven saws can damage viable living cut bone surfaces and should be avoided. In other words, the seat formation may be in the form of a channel, which has an interior surface which provides the concave side of the seat formation; and the guide formation may be a slot in the channel for receiving a saw blade while it initiates the making of the cut in the bone, the slot extending transversely to the channel. Each slot may have a midpoint, midway between its ends, which is intersected by the longitudinal midline of the channel.

Each saw guide may be straight and may be of metal, eg stainless steel or surgical steel, construction. Each saw guide may be of U-shaped or hollow pan-cylindrical shape, eg semi-cylindrical. Each saw guide may have a single said slot, or a plurality of said slots. Preferably the saw guide or guides together provide a plurality of slots at various inclinations to the polar axes of the saw guides, to permit guiding of a saw at various angles to a long bone to be cut. In a particular embodiment of the invention there may thus be a plurality of said saw guides having said seat formations in the form of channels, at least some of the channels having said slots which, when each channel is viewed from the convex side thereof in a direction perpendicular to the longitudinal midline thereof, are inclined at angles to said longitudinal midline which are different from one another; and there may be a saw guide having a seat formation in the form of a channel which has a plurality of said slots therein, which slots when viewed in a direction perpendicular to the longitudinal midline thereof, are inclined at angles to said longitudinal midline which are different from one another.

Furthermore, a plurality of saw guides may be provided, of various cross-sectional dimensions, to cater for bones of different cross-sectional dimensions or thicknesses, so that there is, for commonly encountered bone sizes, at least one saw guide in the set which can receive a bone to be cut in its interior with a sufficiently close fit.

It will be appreciated that, when the saw guide is part-cylindrical, eg semicylindrical, in shape, any slot of the type in question therein will be able to receive a flat plane intersecting the cylinder of the guide and will follow a path along the surface of the saw guide which is part-elliptical in shape, and each slot is preferably formed so that its center, midway between its ends, is intersected by the short axis of the ellipse of which it forms part. In this case, when the saw guide or guides of the set provide a plurality of slots, the slots may be formed so that the long axes of the ellipse of which they form part, make various acute angles relative to the polar axes of the associated saw guides. These angles may be selected to vary from close to 90°, when the ellipse in question is nearly circular, down to 30° or less, when said ellipse is elongated.

The number of slots provided by the saw guide or guides of the set is conveniently selected to permit guiding of a saw at a series of progressively varying said angles, such that there is a slot suitable for making, for practical purposes, a cut at any desired angle. For example, a total of 5–15, eg 8–10, slots may be provided by the set, whose said angles vary at progressive, eg regular, intervals from slightly more than 90° or slightly less than 90° down to 30°.

Each saw guide should preferably have a pair of axially spaced openings therethrough, for receiving fasteners, such as screws, for fixing the saw guide to a bone to be cut, with the bone in its interior; and at least one end of each saw guide may be graduated by means of a plurality of circumferentially spaced graduations, for assisting in rotation of the guide around a bone in its interior by a desired or predetermined angle, eg with reference to an anterior longitudinal reference line marked for this purpose on the bone being cut.

In another embodiment, the guide formation may be adjustable, conveniently pivotal, relative to the seat formation. The saw guide may then have markings to assist in adjustment in use and locking means to lock the guide formation in an adjusted position. In this embodiment the guide formation may be adjustable relative to the channel, by being pivotally connected to a longitudinal extension of the channel which projects at a central position from an end of the channel, about a pivot axis which is centrally located, in line with the longitudinal midline of the channel, and which extends radially relative to the channel, the guide formation being located radially outwardly of the channel, on the convex side of the channel, and being lockable relative to the extension of the channel to prevent relative rotation therebetween, the guide formation having a groove for receiving a saw blade while it initiates the making of the cut in the bone, the groove facing and opening in the same direction as that towards which the concave side of the channel faces. As indicated above, there may be a plurality of said saw guides having seat formations in the form of channels, at least some of which seat formations have cross-sections of different sizes, for receiving long bones of different thicknesses.

Each drill guide may similarly be of metal such as stainless steel or surgical steel; and its anchor may be in the form of a flat anchor plate. The drill guide may have a single bit guide which has a single passage and which is adjustable relative to the plate, or it may have a plurality of parallel passages, being fixed relative to the plate, each passage being aligned perpendicular to the plate. The bit guide may be connected to the anchor by a bridge or stem which may be of flattened shape, the plate being connected to the stem at an edge of the anchor plate, with a 90° corner defined between the anchor plate and the plane of the stem, the anchor plate preferably being elongate rectangular in outline and connected at a long edge Thereof to an edge of a thickened end portion of the stem.

In a particular embodiment, the drill guide may have an anchor in the form of a flat anchor plate, the anchor plate being connected to the bit guide by a bridge and the guide path of the bit guide being an elongated passage through the bit guide for receiving a drill bit in its interior, the passage through the drill guide being aligned perpendicular to the anchor plate. In this embodiment the bridge may be an elongated stem at opposite ends of which the anchor plate and bit guide are located, the anchor plate and bit guide projecting transversely to the stem, to the same side of the stem, so that they oppose each other.

By way of development, the flat anchor plate may be adjustably securable to the thickened end portion. Adjustability may be obtained by providing a plurality of apertures in each of a pair of rows in the anchor plate, and, correspondingly a pair of apertures in the thickened end portion. Selected apertures can then be indexed with the apertures in the end portion, and the components secured by means of fasteners such as screws, nut-and-bolt arrangements, or the like. In other words, the degree to which the anchor plate projects to said side of the stem may be adjustable, the anchor plate being movable relative to the stem in a direction perpendicular to the passage through the drill guide and being lockable relative to the stem to prevent relative movement therebetween.

The bit guide may be in the form of a block connected to a face of the stem at the end of the stem remote from the anchor plate, on the same side of the stem as that towards which the anchor plate projects. The set may comprise a single drill guide or, conveniently, a plurality thereof, having respective stems of different lengths. When a drill guide has a bit guide with several passages and a flat stem as described above, the passages may be arranged side-by-side in a series which extends in a direction perpendicular to the stem such that a drill bit can be guided by selected passages to drill centrally positioned passages in bones of various thicknesses. In other words, the bridge may be in the form of a straight elongated flat planar strip, the bit guide being in the form of a post having a plurality of said bit guide passages therethrough, the anchor plate and post projecting in a direction perpendicular to the plane of the strip, and the bit guide passages being arranged in a series which extends lengthwise along the post, to permit a bit guide passage to be selected which permits drilling of a passage in the bone which is as far as possible precisely centrally located in the bone.

The set of instruments may further include one or more internal bone fixation devices, such as screws or bolts, eg lag screws or lag bolts, each for insertion into a passage formed by a drill guided by a said drill guide in bone fragments which have been partially severed by a saw guided by a said saw guide, for compressing the bone fragments together after they have been separated by the saw and rotated into a desired alignment, around an axis provided by said screw or bolt, the screw or bolt intersecting both cut surfaces centrally and perpendicularly.

The set of instruments may further comprise at least one screw-driver or bolt-driver for driving a said screw or bolt; and the set may comprise at least one suitable external bone fixation device for securing the bone fragments together after they have been compressed together by the screw or bolt.

The invention extends also to a saw guide as described above; and to a drill guide as described above.

Further according to the invention there is provided a method of carrying out an osteotomy procedure, to reduce misalignment between portions of a long bone, the method comprising the steps of:

making an oblique cut through the bone at or adjacent the position where the misalignment portions intersect each other, to divide the bone into two fragments;

bolting the fragments loosely to each other to provide an axis about which the fragments can be rotated relative to each other to reduce the misalignment;

rotating the fragments relative to each other about said axis to reduce the misalignment; and bolting the fragments tightly to each other so that the opposed cut ends of the fragments are clamped to each other.

Making the cut may be by sawing the method including the steps of connecting a saw guide to the bone and guiding a saw by means of the saw guide while the saw initiates the making of the cut. In particular, making the cut may take place in two stages, namely an initial cutting stage in which the cut is partially made and a final cutting stage in which the cut is completed, bolting the fragments loosely together taking place by drilling a passage in bone, after the initial cutting stage and before the final cutting stage, so that the passage passes through both bone portions and intersects the part of the cut made during the initial cutting stage and is perpendicular thereto, and by inserting a bolt into the passage, loosely to bolt said portions to each other, the final cutting stage taking place after the bolting and acting to separate the bone into said fragments. These fragements are then rotated relative to each other about the axis provided by the bolting.

The method may include the step of guiding a drill bit by means of a drill guide while the bit is drilling the passage, the method including inserting part of the drill guide into the partially made cut, to align the drill guide, and hence the drill bit, relative to the partially made cut, so that the bit is perpendicular to the partially made cut; and it may include the step of, after the fragments are bolted tightly to each other, of locking the bone fragments against relative rotation therebetween. Locking the fragments against relative rotation therebetween may be by inserting a locking member into the bone fragments so that the locking member intersects and bridges the cut; and inserting the locking member may be by forming a slot in the bone fragments which intersects the cut, and inserting a locking member in the form of a locking plate into the slot.

BRIEF DESCRIPTION OF THE DRAWINGS

Thus, the method described above can conveniently be carried out using the set of instruments, in particular the saw guide and drill guide, of the present invention.

The invention will now be described, by way of example, with reference to the accompanying diagrammatic drawings, in which.

DESCRIPTION OF THE PREFERRED EMBODIMENTS

Figure 1:
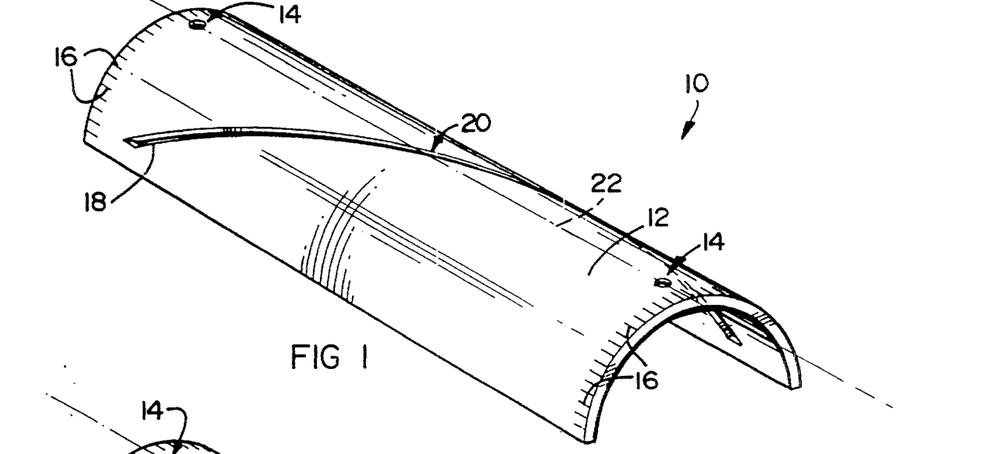
FIG. 1 shows a schematic three-dimensional view of a saw guide forming part of a set of surgical instruments according to the invention.

In FIG. 1 of the drawings, reference numeral 10 generally designates a saw guide according to the invention. The guide 10 has a seat formation in the form of a channel having a body 12 which is of hollow semicylindrical shape, having a semi-circular cross-section. The body 12 has, on its longitudinal mid-line, a pair of longitudinally spaced screw holes 14, respectively adjacent its ends, and at each end thereof, a series of circumferentially spaced graduations 16.

The body 12 is further provided with a slot 18 therethrough, the slot following an elliptical path along the surface of the body, so that the slot 18 can receive and guide a flat planar saw blade along a flat plane intersecting the body 12. The slot 18 is arranged so that it has a midpoint at 20, midway between its ends, which is intersected by the midline 22 of the body 12 extending between the holes 14. If the guide 10 is viewed in a direction parallel to a radius of the body passing through the midpoint at 20, the slot will make an acute angle of about 60° relative to the polar axis of the body 12, said radius coinciding with the short axis of the elliptise of the path followed by the slot. The slot 18 is about 1 mm in width, for use with a hacksaw blade of about 0,5 mm thickness, to provide a working clearance.

Figure 2:
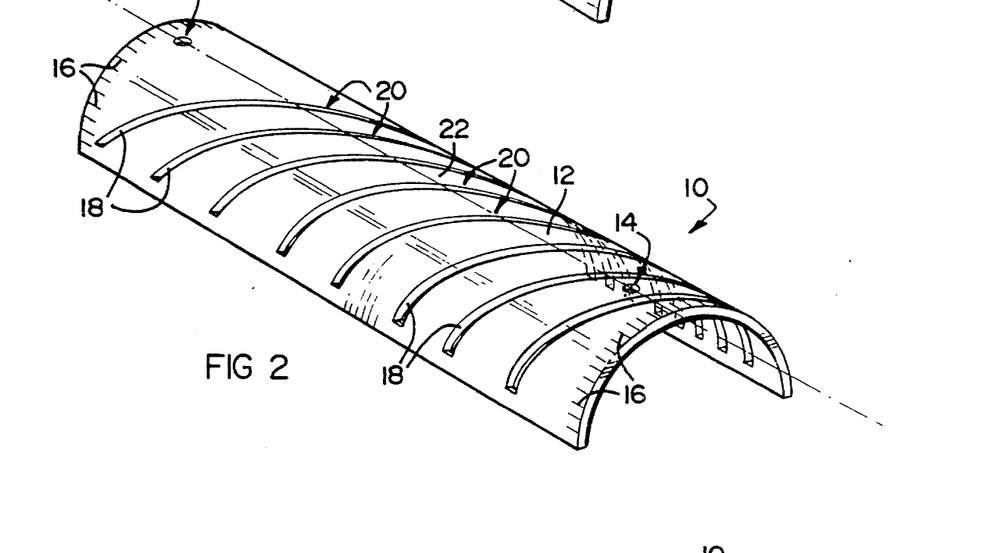
FIG. 2 shows a similar view of another saw guide according to the invention.
Figure 3:
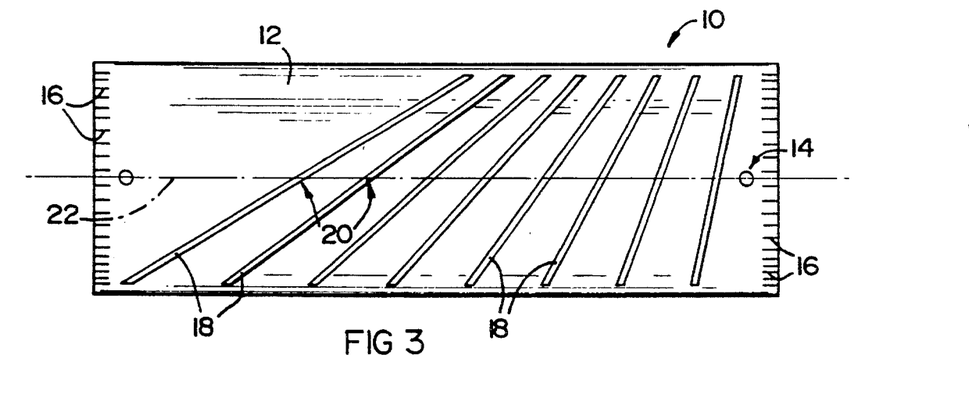
FIG. 3 shows a schematic plan view of the guide of FIG. 2.

In FIGS. 2 and 3 the same reference numerals are used for the same parts as in FIG. 1, and the construction shown in FIG. 2 is the same as that of FIG. 1, except that there are eight slots 18 arranged in series instead of the one shown in FIG. 1. Each slot 18 in FIG. 1 follows an elliptical path of the type described above with reference to FIG. 1 selected such that, when the guide 10 is viewed in a direction parallel to the radii passing through the midpoints 20 of the slots 18, the acute angles made by the slots 18 relative to the polar axis of the body 12 will vary from about 60° for the slot 18 at the one end of the series to a little less than 90° at the other end of the series, the angles varying progressively at regular intervals of about 4°–5° from 60° to close to 90°.

Figure 4:
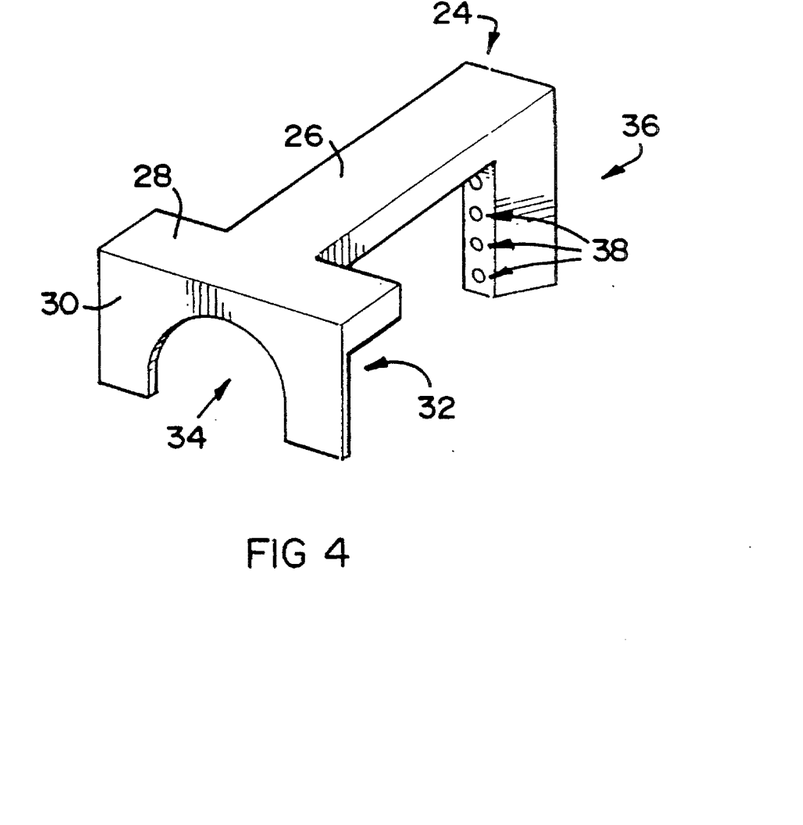
FIG. 4 shows a three-dimensional view of a drill guide according to the invention.
Figure 5:
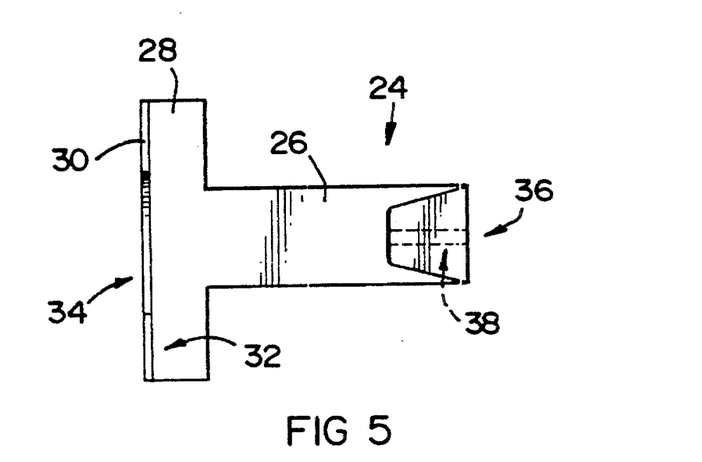
FIG. 5 shows an underside plan view of the guide of FIG. 4.

Turning to FIGS. 4 and 5, reference numeral 24 generally designates a drill guide according to the invention. The guide 24 comprises a flattened, elongated stem 26 having a thickened end portion 28 at one end thereof, of increased width relative to the remainder of the stem 26. An anchor plate 30, which is elongate rectangular in outline, is fast at one of its longer edges to the end edge of the portion 28, at one end of the stem 26, so that it projects at a 90° corner at 32, to one side of the stem 26. The opposite long edge of the plate 30 has a curved indentation 34.

At its opposite end the stem 26 is provided with a bit guide 36 in the form of a block-like post 36 having a plurality of straight parallel passages 38 therethrough. The post 36 projects to the same side of the stem 26 as the plate 30; and the passages 38 are parallel to the stem 26, extending in the long direction of the stem 26. The passages 38 are spaced in series parallel to one another, and perpendicular to the plate 30, the series extending in a direction perpendicular to the stem 26. The passages 38 are directed towards the indentation 34 which is intersected by projections of the passages 38.

The guides 10 and the guide 24 are of surgical stainless steel.

Figure 6:
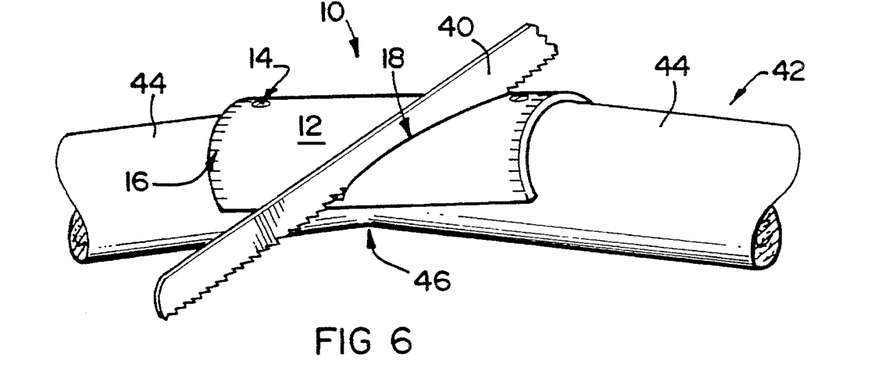
FIG. 6 shows a three dimensional views of the saw guide of FIG. 1 in use.
Figure 7:
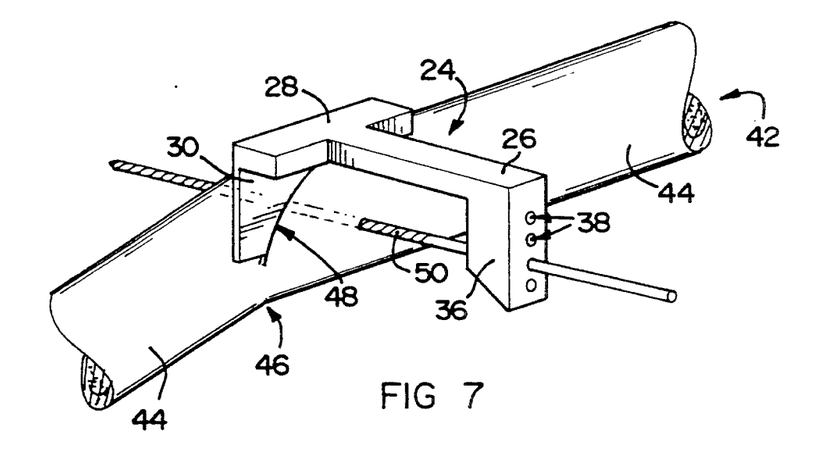
FIG. 7 shows a three dimensional view of the drill guide of FIGS. 4 and 5 in use.

In FIG. 6 the saw guide 10 of FIG. 1 is shown in use guiding a saw blade 40 of about 10–12 mm width and 0,5 mm thickness during the cutting of a long bone 42 to be straightened and having two misaligned portions 44, intersecting at 46, whose misalignment is to be reduced. The guide 10 is first attached to the bone 42 by at least one, and if practically possible by a pair of screws (not shown) passing through the holes 14. A cut 48 is then made by the saw 40 partially (eg about ¾ of the way) through the bone 42. The saw guide 10 and saw 40 are then removed, and the drill guide 24 is inserted as far as possible into the cut 48 (see FIG. 7), and is manipulated along the cut 48 so that one of the passages 38 extends along a line which intersects the cut 48, perpendicular thereto, as close as possible to the center of area of the cut in the bone 42 which would be made by projecting the cut 48 all the way through the bone 42 to cut it into two fragments 44, corresponding to the misaligned portions 44. A drill bit 50 is then guided by this passage to drill a passage through the bone and intersecting the cut 48.

The drill guide 24 is then removed and a lag bolt (see 90 in FIG. 14) is inserted, using a suitable driver, along the drilled passage to connect the portion 44 on one side of the cut 48 to the portion 44 on the other side thereof, to bolt the bone portions on opposite sides of the cut loosely together. The remainder of the cut 48 is then made with the saw 40, using the initial part of the cut 48 to guide the saw 40, until the bone 42 is finally cut into two fragments.

The bone fragments 44, loosely bolted together by the lag bolt 90, are then rotated relative to each other about an axis provided by the polar axis of the lag bolt (see 90 in FIG. 14) by a desired angle, to straighten the bone, after which said bolt is tightened to clamp said fragments together. The lag bolt has a spring washer which is stressed to hold the bone fragments loosely together to permit the rotation.

From the aforegoing it will be appreciated that the guides 10 and 24 are used in surgery to reduce and preferably correct misalignment between portions 44 of, and hence straighten, a long bone 42 which has a bend or kink at 46 and is not straight. Known methods are used to determine the location of the cut 48 and its desired inclination relative to the length of the bone, as well as the degree of rotation of the bone fragments required best, or at least adequately, to straighten the bone. At the conclusion of the surgery a suitable external bone fixation device (not shown) can optionally be used to supplement the lag bolt to clamp the bone fragments together, this device being removed after the surgery has healed sufficiently, the lag bolt being left permanently in position.

Figure 8:
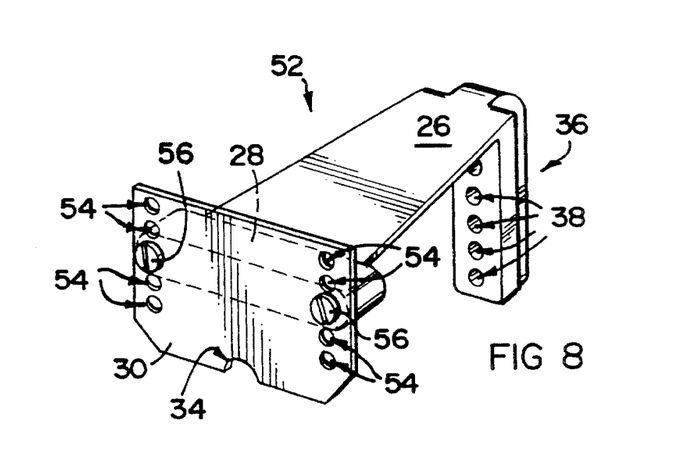
FIG. 8 corresponds to FIG. 4 but shows another embodiment of a drill guide.

By way of development, with reference to FIG. 8, a drill guide 52 similar to the drill guide 24 of FIGS. 4 and 5 is now described. The drill guides are similar and like reference numerals refer to like features. The drill guide 52 is not again described in detail and emphasis will merely be placed on the differences between the drill guides.

The anchor plate 30 is rendered adjustable relative to the stem 26 by having it separable from the thickened end portion 28, by providing, along sides of the anchor plate 30, adjustment apertures 54 in rows parallel to each other and parallel to the adjustment apertures 38 in the bit guide 36. Corresponding apertures in the form of threaded sockets are provided in the thickened end portion 28. The degree to which the operative portion of the anchor plate 30 projects to the same side of the stem 26 as the bit guide 36 can be adjusted by selectively indexing a pair of apertures 31 with the apertures in the thickened end portion 28 and securing the anchor plate 30 to the thickened end portion 28 by way of suitable fasteners such as screws 56.

The curved indentation 34 is substantially smaller than that of the FIG. 4 embodiment and is intended merely to be passed the leading end of the bit with operating clearance in use.

Use of the drill guide 52 is similar to that described for the drill guide 24.

Figure 9:
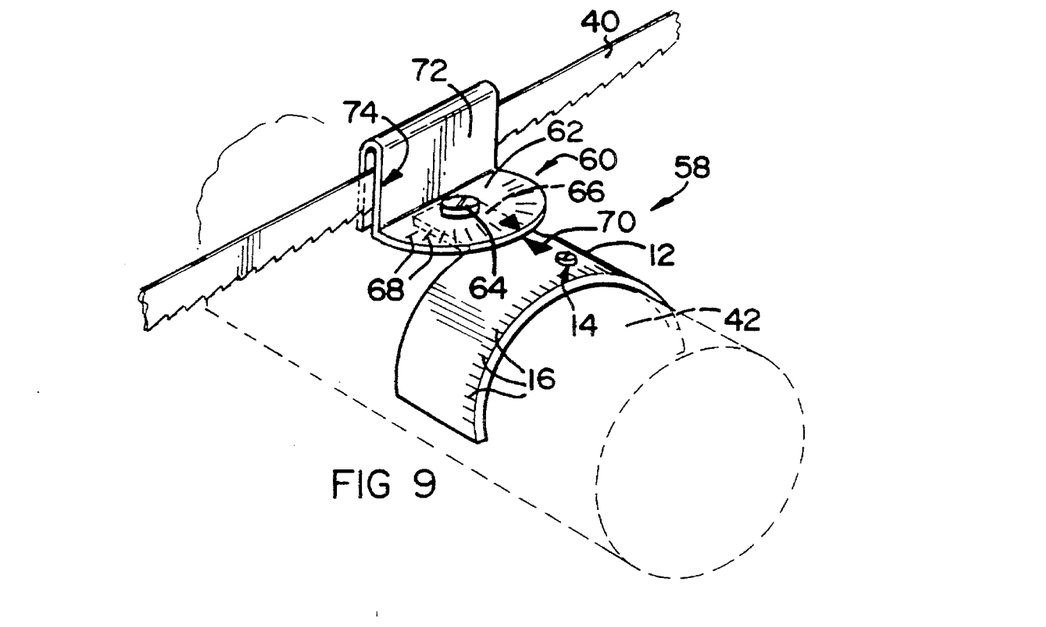
FIGS. 9 and 10 show, respectively in three dimensional view and in plan view, another embodiment of a saw guide, which is adjustable, in use.
Figure 10:
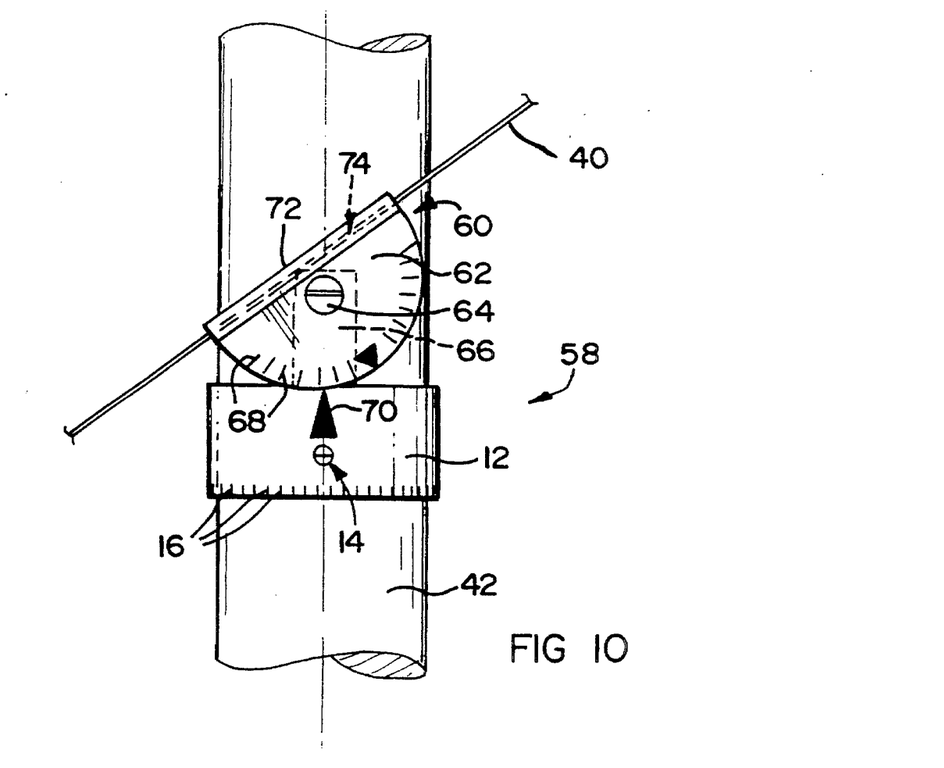

Further by way of development, and with reference to FIGS. 9 and 10, an adjustable saw guide is now described. The adjustable saw guide, generally indicated by reference numeral 58, is in many respects functionally similar to the saw guide 10 of FIG. 2 and like reference numerals refer to like features.

The saw guide 58 has a short semi-cylindrical seat formation in the form of a short channel 12 providing a seat within which a long bone 42 to be severed is seated in use. The seat formation 12 has an aperture 14 and graduations 16 similar to those described for the guide 10 of FIG. 2. Such graduations are used to orient the seat formation appropriately to ensure that the cut will be appropriately oriented.

The saw guide 58 further has adjustable guide means generally indicated by reference numeral 60. The guide means 60 comprises a generally semi-circular arcuate base in the form of a protractor 62 of about 20 mm radius which is pivotally mounted about an axis provided by a tightenable screw 64 on a projection 66 of the seat formation 12 provided for that purpose. Instead, it may be pivotal about an axis provided by a rivet and may then have separate locking means. It further has graduations 68 which show up to 90° on opposite sides of a central point and which are used in association with a pointer 70 centrally fixed to the seat formation 12 to adjust the guide means. A saddle formation 72 is integral with the arcuate base 62 and defines a groove 74 having a width of about 1 mm and a depth of 15–20 mm, within which a saw blade 140 is slidably receivable. The groove 74 faces and opens in the same direction as the concave side of the seat formation 12.

In use, the adjustable guide means 60 is adjusted to a desired angle by pivoting it appropriately and tightening the screw 64. The seat formation 12 is then positioned on the long bone 42 such that the groove 74 registers with the position where the cut is to be made. The seat formation 12 is fixed to the long bone 42 by means of a screw extending through the aperture 14. The saw blade 40 is positioned within the groove 74 with its serrations directed towards the bone 42, and the cut 48 can be made.

The saw guide 58 has the advantage that it can be adjusted, to either side, between a condition in which the groove 74 is perpendicular to the axis of the seat formation 12 and a condition in which the groove 74 is aligned at a selected small angle, which may be of the order of about 20° to 30°, to said axis. Thus, the adjustable saw guide 58 can be employed instead of a plurality of saw guides such as the saw guides of FIGS. 1 and 2. It further has the advantage, if desired, that the angle at which the cut is made can be adjusted in stepless fashion.

Figure 11:
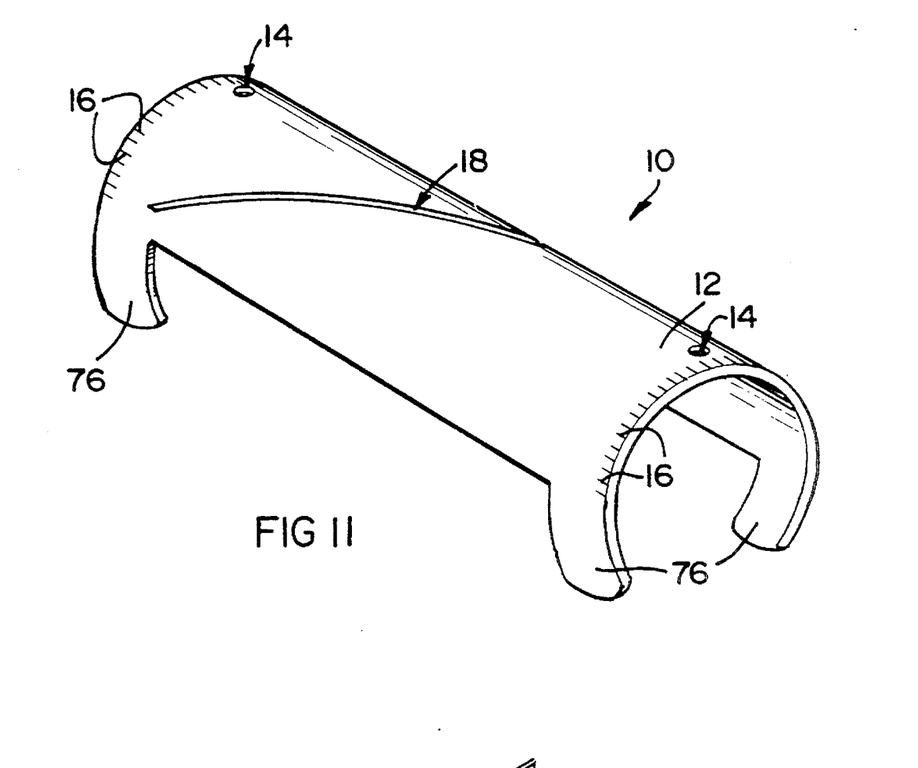
FIG. 11 shows a view, similar to FIG. 1, of a development of the saw guide of FIG. 1.

In FIG. 11 the same parts are designated by the same reference numerals as in FIG. 1. The only material difference between the saw guide 10 of FIG. 11 and that of FIG. 1 is that, at each end thereof, the body 12 has a pair of resiliently flexible clip-like circumferential extensions 76. The pair of clips 76 at each end of the body 12 together form a clamp at that end of the body 12 for clipping to and clasping a long bone 42 (see FIG. 6) seated in the body 12.

Figure 12:
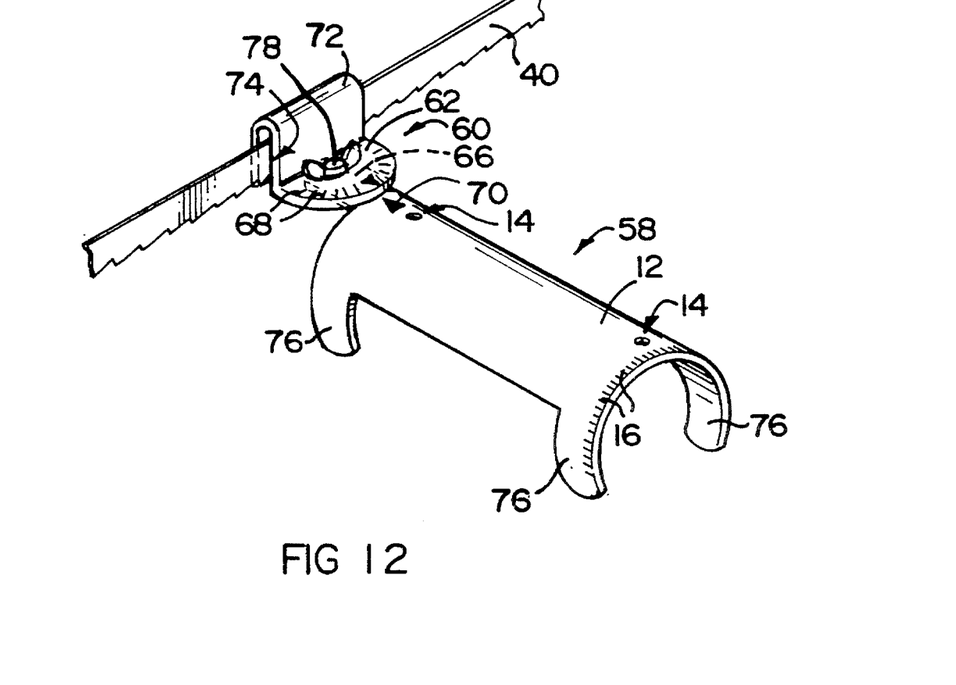
FIGS. 12 and 13 show views, similar to FIG. 9, of a development of the saw guide of FIG. 9.
Figure 13:
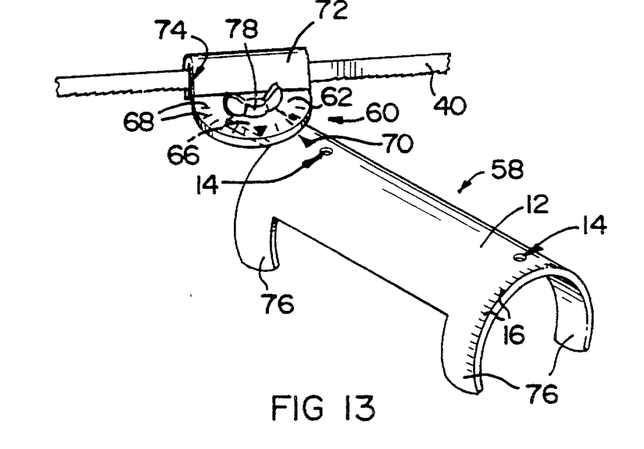

Similarly, in FIGS. 12 and 13, the same reference numerals refer to the same parts as in FIG. 9, unless otherwise specified. In FIGS. 12 and 13, the body 12 of FIG. 11 merely replaces the short channel seat formation 12 of FIG. 9, and the screw 64 of FIG. 9 is replaced by a wing-nut 78.

Use of the guides 10 and 58 of FIG. 11, and of FIGS. 12 and 13 is substantially identical to use respectively of the guides 10 and 58 of FIGS. 1 and 9, except that the clips 76 at each end of the body 12 are used to clamp a bone 42 (FIGS. 6 and 9) seated in the body 12.

Figure 14:
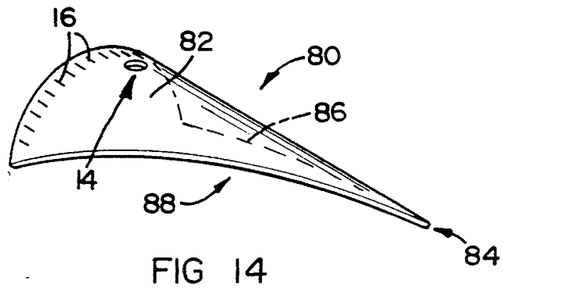
FIG. 14 shows a view, similar to FIG. 1, of a modified form of the saw guide of FIG. 1.

Turning to FIG. 14, a saw guide designated 80 is shown which can be regarded as having a body 82 which is tapered and part-hollow cylindrical and equivalent to half of the body 12 of a guide 10 of the type shown in FIG. 1. The graduations 16 are shown at the large end of the guide 80, which end is semi-circular in shape. The body 82 tapers away from the semi-circular end to a point or apex at 84. The tapering body 82 has an edge 86 parallel to the axis of the body, and an inclined edge 88 corresponding to the slot 20 of FIG. 1. Use of the guide of FIG. 14 is similar to that of FIG. 1 except that the saw blade 40 (see FIG. 6) is aligned with and held up against the edge 88 of the guide 80 instead of being located in the slot 20 (FIG. 6).

Figure 15:
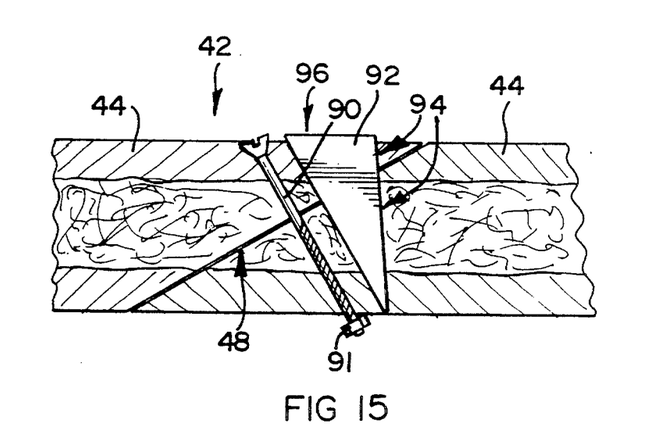
FIG. 15 shows, in schematic sectional side elevation, a pair of bone fragments clamped together at the end of an osteotomy procedure in which the set of instruments of the present invention has been used.

In FIG. 15 a straightened bone is designated 42 and its fragments 44 are shown bolted together by a .lag bolt 90 having a spring washer (not shown) at its head as described above, and a nut 91. Naturally, the spring member can instead be at the nut 91 rather than at the bolt head. A locking member 92 is shown inserted in a slot 94 which extends through the bone 42 substantially from one side thereof to the other, and which passes through both fragments 44 and intersects the cut 48. The member 92 is shown to be in the form of a tapering strip of surgical steel plate about 10 mm in width, tapering from a broad end 96 which is about 10–12 mm in width. To form the slot 94 an oscillating saw is used and the member 92 is driven or pressed into the slot 94, to occupy it. A so-called Tuke oscillating Saw, having a tapered blade, is used to form the slot, with a taper and thickness corresponding to that of the member 92.

After sufficient healing has taken place, the member 92 and lag bolt 90 can be removed. Naturally, instead of the lag bolt as illustrated, a lag screw can be used in similar fashion.

An advantage of the invention is that use of the set of instruments totally avoids the use of a bone graft, so that bone necrosis is reduced, if not avoided, and delays in vascularization and ossification by invading osteogenesis are reduced. Location of the cut can be judged by eye by an experienced surgeon at one extreme, or, at the other extreme, computer programmes are available to determine its exact position, allowing the surgeon rapidly to select the appropriate saw guide 10 (FIG. 1) or slot 24 (FIG. 2), or to select the appropriate saw guide setting (FIG. 9). Similar considerations apply to the drill guide which allows selection of the appropriate passage 38 (FIG. 5) and indeed adjustment thereof (FIG. 8).

In particular, the set of instruments permits the surgical procedure to be carried out, importantly, both quickly and accurately and, furthermore permits procedures to be carried out where bone fragment union can take place within days by virtue of the clamping by means of the lag bolt 90. Use of the bolt 90 and locking member 92 provide an immediate union which is strong and stable, and which, in appropriate cases, can permit a patient to be mobile virtually immediately. Furthermore the procedures using the set of instruments are of relatively low invasiveness and duration and post-operative treatment is, in principle, confined to the simple removal, after several weeks, of the lag bolt 90 and locking member 92, which removal is quick and easy.

I claim:

1. A method of carrying out an osteotomy procedure to reduce misalignment between portions of a long bone, the method comprising the steps of:

making an oblique cut through the bone at or adjacent the position where the misalignment portions intersect each other, to divide the bone into two fragments;

bolting the fragments loosely to each other to provide an axis about which the fragments can be rotated relative to each other to reduce the misalignment;

rotating the fragments relative to each other about said axis to reduce the misalignment; and bolting the fragments tightly to each other so that the opposed cut ends of the fragments are clamped to each other.

2. A method as claimed in claim 1, in which making the cut is by sawing, the method including the steps of connecting a saw guide to the bone and guiding a saw by means of the saw guide while the saw initiates the making of the cut.

3. A method as claimed in claim 2, wherein the saw guide is in the form of a channel having an outer side which is convex and a concave side on its interior surface abutting the bone.

4. A method as claimed in claim 1, in which making the cut takes place in two stages, namely an initial cutting stage in which the cut is partially made and a final cutting stage in which the cut is completed, bolting the fragments loosely together taking place by drilling a passage in bone, after the initial cutting stage and before the final cutting stage, so that the passage passes through both bone portions and intersects the part of the cut made during the initial cutting stage and is perpendicular thereto, and by inserting a bolt into the passage, loosely to bolt said portions to each other, the final cutting stage taking place after the bolting and acting to separate the bone into said fragments.

5. A method as claimed in claim 4, which includes the step of guiding a drill bit by means of a drill guide while the bit is drilling the passage, the method including inserting part of the drill guide into the partially made cut, to align the drill guide, and hence the drill bit, relative to the partially made cut, so that the bit is perpendicular to the partially made cut.

6. A method as claimed in claim 1, which includes the step, after the fragments are bolted tightly to each other, of locking the bone fragments against relative rotation therebetween.

7. A method as claimed in claim 6, in which locking the fragments against relative rotation therebetween is by inserting a locking member into the bone fragments so that the locking member intersects and bridges the cut.

8. A method as claimed in claim 7, in which inserting the locking member is by forming a slot in the bone fragments which intersects the cut, and inserting a locking member in the form of a locking plate into the slot.

* * * * *

UNITED STATES PATENT AND TRADEMARK OFFICE
CERTIFICATE OF CORRECTION

PATENT NO. : 5,470,335

DATED : November 28, 1995

INVENTOR : Du Toit

It is certified that error appears in the above-identified patent and that said Letters Patent is hereby corrected as shown below:

Column 3, line 24, "edge Thereof" should be --edge thereof--.

Column 4, line 54, "fragements" should be --fragments--.

Column 9, line 9, "oscillating Saw," should be --oscillating saw,--.

Signed and Sealed this

Third Day of September, 1996

Attest:

BRUCE LEHMAN

Attesting Officer

Commissioner of Patents and Trademarks